US010379014B2

(12) United States Patent
Calatzis et al.

(10) Patent No.: US 10,379,014 B2
(45) Date of Patent: Aug. 13, 2019

(54) SYSTEM AND METHOD FOR PREPARING A BIOLOGICAL SAMPLE FOR ANALYSIS

(71) Applicant: Roche Diagnostics Operations, Inc., Indianapolis, IN (US)

(72) Inventors: Andreas Calatzis, Rotkreuz (CH); Harald Leyser, Steinefrenz (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/356,694

(22) Filed: Nov. 21, 2016

(65) Prior Publication Data

US 2017/0146437 A1    May 25, 2017

(30) Foreign Application Priority Data

Nov. 23, 2015 (EP) .................................... 15195869

(51) Int. Cl.
*G01N 1/00* (2006.01)
*G01N 1/30* (2006.01)
*G01N 1/31* (2006.01)
*G01N 35/00* (2006.01)

(52) U.S. Cl.
CPC ............... *G01N 1/30* (2013.01); *G01N 1/312* (2013.01); *G01N 35/00009* (2013.01); *G01N 35/00029* (2013.01)

(58) Field of Classification Search
CPC ...................................................... G01N 1/00
See application file for complete search history.

(56) References Cited

U.S. PATENT DOCUMENTS

| 3,851,156 | A | 11/1974 | Green |
| 3,991,705 | A | 11/1976 | Adler |
| 5,120,506 | A * | 6/1992 | Saito ..................... B01L 1/02 34/625 |
| 5,508,200 | A | 4/1996 | Tiffany et al. |
| 8,048,245 | B2 | 11/2011 | Angros |
| 8,679,853 | B2 | 3/2014 | Bhullar et al. |
| 9,017,610 | B2 | 4/2015 | Winkelman et al. |
| 9,091,620 | B2 | 7/2015 | Yi |
| 9,463,643 | B2 | 10/2016 | DeJoseph et al. |
| 2005/0003458 | A1 | 1/2005 | Moore et al. |
| 2015/0253224 | A1 | 9/2015 | Liffmann et al. |

(Continued)

FOREIGN PATENT DOCUMENTS

| EP | 0683395 A2 | 11/1995 |
| GB | 1036776 | 7/1966 |

(Continued)

OTHER PUBLICATIONS

Extended European Search Report dated Jun. 1, 2016 in Application No. EP15195869.1, 9 pages.

(Continued)

*Primary Examiner* — Jyoti Nagpaul
(74) *Attorney, Agent, or Firm* — Dinsmore & Shohl, LLP (57) ABSTRACT

A method for preparing a biological sample for analysis is provided that includes moving a continuous substrate film past a sample applicator unit including one or more sample applicators and applying at least one trace of a biological sample to be analyzed onto the continuous substrate film by the sample applicator unit.

20 Claims, 5 Drawing Sheets

(56) References Cited

U.S. PATENT DOCUMENTS

2016/0356682 A1   12/2016   Liffmann et al.

FOREIGN PATENT DOCUMENTS

WO   2008/140969 A1   11/2008
WO   2012/159275 A1   11/2012

OTHER PUBLICATIONS

Adler, et al.; "Fully Automated Preparation of High-Quality Stained Blood Films"; The International Academy of Cyology; vol. 3; No. 3; Sep. 1981; pp. 216-224.
Vickers Cytology Screening Apparatus, Vickers Limited Vickers Instruments, Croydon, Surrey, England, 1968, pp. 1-12.
Boddington, et al.; "Apparatus for Automatic Preparation and Scanning in Cervical Cytology", British Medical Journal, Jul. 15, 1967, pp. 160-161.

* cited by examiner

SYSTEM AND METHOD FOR PREPARING A BIOLOGICAL SAMPLE FOR ANALYSIS

CROSS-REFERENCE TO RELATED APPLICATIONS

The present application claims priority to European Patent Application No. 15195869.1, filed 23 Nov. 2015, the disclosure of which is hereby incorporated by reference in its entirety.

TECHNICAL FIELD

The present disclosure relates to methods for preparing a biological sample for analysis, apparatus for preparing biological samples for analysis, uses of continuous substrate films for preparing a biological sample for analysis, and continuous substrate films configured to receive a trace or traces of a biological sample for analysis.

BACKGROUND

In some analysis systems for analyzing biological samples (e.g., blood samples) a trace of the sample is applied to a microscope slide. This slide is then moved through different stages of an analysis system where the actual analysis process and different pre- and post-processing steps can take place. For instance, the trace of the biological sample can be stained, dried and imaged with a microscope (e.g., to count a number of white blood cells or red blood cells in the trace).

Handling of the microscope slides can, in some examples, require a comparatively complex and thus costly and error-prone handling apparatus.

SUMMARY

It is against the above background that the embodiments of the present disclosure provide certain unobvious advantages and advancements over the prior art. In particular, the inventors have recognized a need for improvements in systems and methods for preparing a biological sample for analysis.

In accordance with one embodiment of the present disclosure, a method for preparing a biological sample for analysis is provided and includes moving a continuous substrate film past a sample applicator unit including one or more sample applicators and applying at least one trace of a biological sample to be analyzed onto the continuous substrate film by the sample applicator unit.

In accordance with another embodiment of the present disclosure, an apparatus for preparing a biological sample for analysis is provided and includes a film transportation device configured to move a continuous substrate film past a sample applicator and the sample applicator unit including one or more sample applicators configured to apply a trace of a biological sample to be analyzed onto the continuous substrate film.

In accordance with still another embodiment of the present disclosure, use of a continuous substrate film in a process for preparing a biological sample for analysis is provided, the biological sample being applied as a trace of a biological sample onto the continuous substrate film by the sample applicator.

In accordance with yet still another embodiment of the present disclosure, a continuous substrate film configured to receive a trace of a biological sample for analysis is provided, the continuous substrate film including a coating applied to a surface of the continuous substrate film onto which the trace of a biological sample for analysis is deposited to improve adherence of the trace of the biological sample.

Although the embodiments of the present disclosure are not limited to specific advantages or functionality, it is noted that, firstly, using a continuous substrate film as a carrier for a trace of a biological sample can simplify the handling apparatus of the analysis system. For instance, the continuous substrate film can be moved continuously through the analysis system by one or more rollers or other film moving devices. This can be less demanding in terms of handling complexity than handling microscope slides in some situations. Handling microscope slides can require actuators adapted to move a slide in two or three orthogonal spatial directions. Analysis systems using a continuous substrate film can supersede at least some of these components. As a result, the analysis systems using a continuous substrate film as carrier for a trace of a biological sample can have a reduced complexity compared to some analysis systems using microscope slides or other sample carriers. This might not only reduce cost of the analysis system but also reduce downtime of the analysis system due to problems of the comparatively complex machinery in some examples. As a consequence, cost of ownership of an analysis system using a continuous substrate film as carrier for a trace of a biological sample can be reduced and the throughput can be increased in some examples.

Secondly, using a continuous substrate film as a carrier for a trace of a biological sample can allow for a sample applicator to remain stationary or only be moved in one direction to adjust a height of the sample applicator over a surface of the continuous substrate film. The continuous substrate film can be moved below the applicator (e.g., by one or more rollers of a continuous substrate film handling device of the analysis system). In some known analysis systems, a sample applicator has to be moved in a relatively complex path in two or even three dimensions. Again, this can require complex mechanical actuators and controllers that might not be necessary in some analysis systems using a continuous substrate film as a carrier for a trace of a biological sample of the present disclosure.

Thirdly, continuous substrate films can be less expensive than some sample carriers used in known analysis systems. In particular, certain analysis systems can require the use of particular comparatively expensive microscope slides.

These and other features and advantages of the embodiments of the present disclosure will be more fully understood from the following description in combination with the drawings and the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present disclosure.

DETAILED DESCRIPTION

In the following detailed description different aspects of methods for preparing a biological sample for analysis, apparatus for preparing biological samples for analysis, uses of continuous substrate films or preparing a biological sample for analysis and continuous substrate films configured to receive a trace of a biological sample for analysis will be discussed in more detail.

A number of terms are used in the present disclosure in a particular way:

The term "continuous substrate film" as used in the present disclosure includes any thin substrate (e.g., the thickness is lower than 1 mm or lower than 500 µm). The attribute "continuous" indicates that an extension of the film in one direction (a direction of transport during analysis) is much larger (e.g., more than 20 times larger or more than 50 times larger) than a second extension of the broad surfaces of the continuous substrate film (i.e., not the direction in which the thickness extends). A microscope slide, on the other hand, is not a continuous substrate film as used in the present disclosure (standard microscope slides are only three time longer than wide).

The continuous substrate films of the present disclosure can be substantially flexible (e.g., repeatably bendable with a bending radius of 10 cm or smaller). The continuous substrate film can include multiple layers in some examples. In a multi-layer continuous substrate film, not all layers have to be continuous as defined in the present disclosure. For instance, a continuous base layer can carry a non-continuous upper layer applied to a continuous base layer in one example.

The terms "patient sample" and "biological sample" refer to material(s) that may potentially contain an analyte to be analyzed. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. In other examples, the patient sample can include a concentrated or diluted form of said fluids.

The biological sample can be pretreated prior to use, such as preparing plasma from blood, diluting viscous fluids, lysis or the like. Methods of treatment can involve filtration, distillation, concentration, inactivation of interfering components, and the addition of reagents. A biological sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

In some examples, the apparatus of the present disclosure can include an analyzer operable to determine via various chemical, biological, physical, optical or other technical procedures a parameter value of a biological sample or a component thereof deposited onto a continuous substrate film. An analyzer may be operable to measure said parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types.

In other examples, the methods and apparatus of the present disclosure can be configured to determine one or more primary or derived parameters of the biological sample. In some examples, the biological sample can include blood or a constituent of blood. The primary and derived measurements for a sample including blood or a constituent of blood can include: i) red blood cell (RBC) count, hemoglobin (Hb), hematocrit (Hct), red blood cell indices (mean corpuscular volume, MCV, mean corpuscular hemoglobin, MCH and mean corpuscular hemoglobin concentration MCHC), red blood cell distribution width, enumeration of other red blood cells including reticulocytes and nucleated red blood cells, and red blood cell morphology; ii) white blood cell (WBC) count and WBC "differential" count (enumeration of the different normal white blood cell types, including neutrophils, lymphocytes, eosinophils, basophils and monocytes, and the probable presence of other normal and abnormal types of WBC that are present in various disease conditions); iii) platelet count, platelet distribution widths and other features of platelets including morphological features; and iv) other abnormal cells or other unusual cells or cellular components that may be in circulating blood. These parameters can be determined based on chemical, biological, physical, optical measurements performed by respective detectors from the sample trace on the continuous film by the apparatus of the present disclosure.

For instance, in the case of analyzing blood or bone marrow, the apparatus of the present disclosure can prepare a trace of blood or bone marrow on a continuous substrate film and optionally capture one or more images of the film. The images may be later used for performing various tests that provide for a count of various cell types, or an assessment of the morphology of the cells. One example is a complete blood count (CBC) including image-based counting and assessment of the morphology of the formed elements of blood, including red blood cells (RBCs), white blood cells (WBCs), and platelets.

The apparatus and methods of the present disclosure can include applying a thin layer of cells (e.g., substantially a monolayer of cells) onto a continuous substrate film that enables assessment of certain cell types (e.g., abnormal and immature WBCs that are found in cases of abnormal bone marrow function including hematological malignancies).

As used in the present disclosure, the phrase "substantially a monolayer" includes films that are a complete monolayer of cells or a layer at least including portions that are a monolayer of cells (e.g., 20% or more of the film's surface consists of a monolayer). In some examples, layer being "substantially a monolayer" may have regions where there is some overlap of cells, for example, at particular locations on the edges of the traces including the cells that are laid down as the continuous substrate film is moved past the applicator.

Aspects of the present disclosure are effective at preserving cell morphology. This may be important for patients with hematological malignancies such as chronic lymphocytic leukemia (CLL) or acute myeloid leukemia (AML). The systems and processes for creating a thin layer of cells, typically substantially a monolayer of cells, from body fluid may enable detection of a larger number of morphologically well preserved blast cells and other immature or fragile cells. This would allow their more accurate recognition at an earlier stage of the leukemic or other disease process. Certain aspects of the present disclosure provide for preparing a substantially uniform distribution of cells across a test area of a continuous substrate film.

Aspects of this disclosure may relate to the application of cells from body fluids to a continuous substrate film and include possibly mixing the cells contained in the body fluid with a diluent, collecting a sub-sample (aliquot) of a known volume from the solution, and then depositing the aliquot onto the continuous substrate film using a dispensing device or applicator. The cells may also be stained. The stained cells on the continuous substrate film may be counted and examined by an automated imaging system utilizing a computer or viewed by manual microscopic examination. Digital images may be shown on a computer display to reduce the need for manual microscopic review.

In accordance with an embodiment of the present disclosure, the methods can include one or more of the steps of: collecting cells from a body site, placing the cells into a preservative solution, mixing the cells in the solution to assure a homogeneous distribution, collecting an aliquot of known volume from the preservative solution and then depositing the aliquot onto a continuous substrate film using an applicator. The cells may be fixed, stained, or allowed to air dry, depending on the examination that is anticipated. The continuous substrate film containing the specimen may be used for either manual microscopic examination, or be examined by an imaging stage that can enumerate the different types of cells that are present on the continuous substrate film.

For example, an embodiment of the present disclosure may be used to determine the number of cells in a sample of the cervix that are infected by the Human Papilloma Virus (this may indicate the viral burden, which is a prognostic factor to assess if an abnormality may progress, remain stable, or regress). Examples of the present disclosure may be able to determine how many viral or infected cells are in the sample. Additionally, certain examples of the present disclosure may be able to determine the differential cell count in a non-gynecologic sample collected from a body cavity effusion. In further examples, the system or method could determine that there is a large number of acute inflammatory cells in a sample (which the system or method may use to determine the presence of a bacterial infection). Similarly, if an embodiment of the present disclosure determined there were a high number of lymphocytes in a particular sample this may suggest a viral infection, autoimmune disease, or tuberculosis.

After having discussed several general aspects of the present disclosure, several example apparatus and method will be discussed subsequently. Firstly, different aspects of an apparatus and a method for preparing a biological sample for analysis will be discussed in connection with FIG. 1 and FIG. 2. Subsequently, alternative and additional aspects of apparatus and methods for preparing a biological sample for analysis will be discussed in connection with FIG. 3 to FIG. 5.

Figure 1:
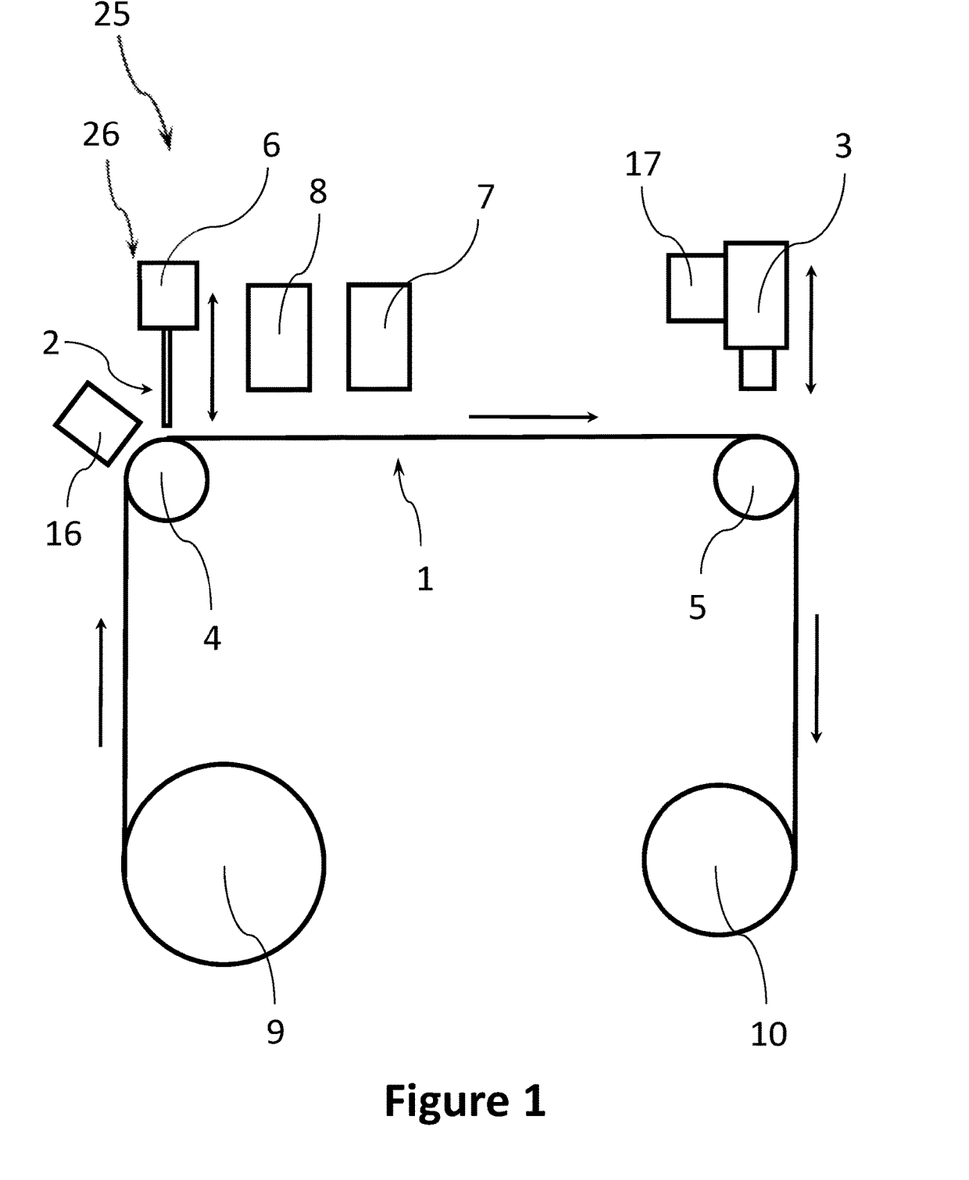
FIG. 1 illustrates an example apparatus for preparing a biological sample for analysis according to an embodiment of the present disclosure.

FIG. 1 illustrates an example apparatus for preparing a biological sample for analysis according to an embodiment of the present disclosure. The apparatus 25 includes a film transportation device 20 configured to move a continuous substrate film 1 past a sample applicator unit 26 including a sample applicator 2, the sample applicator unit 26 being configured to apply a trace of a biological sample to be analyzed onto the continuous substrate film 1.

As can be seen in FIG. 1, the film transportation device 20 includes a plurality of rollers 4, 5, 9, 10 configured to move the continuous substrate film 1. Even though four rollers 4, 5, 9, 10 are depicted in FIG. 1, it is clear that the transportation device 20 can include any suitable number of rollers to move the continuous substrate film, along a predetermined transport path. In one example, the transport path is folded one or several times. This can make the apparatus 25 more compact in some examples.

Alternatively or in addition, the transportation device 20 can include other components than rollers that affect movement of the continuous substrate film 1. For instance, the transportation device 20 can include one or more linear actuators configured to engage with the continuous substrate film 1 and move the continuous substrate film 1, for example, to deflect the continuous substrate film 1 in a particular direction such as in the direction of a container of fluid so as to cause the film to be submerged in the fluid as it passes through the container. In addition or alternatively, the transportation device 20 can include one or more rotational actuators other than rollers to engage with the continuous substrate film 1 and to move the continuous substrate film 1 (e.g., a moving belt).

In the example of FIG. 1, the continuous substrate film 1 is provided from a supply roll 9 and received on a waste roll 10 after the analysis process has taken place. The apparatus of the present disclosure can process the continuous substrate film 1 in a roll-to-roll process. However, in other examples the continuous substrate film 1 can be provided from or received by different apparatus. In one example, the continuous substrate film 1 can be directly guided in a waste bin or other compartment after the analysis process has taken place. In another example, the apparatus can include a cutting stage configured to cut the continuous substrate film in a plurality of shorter parts (e.g., downstream of an imaging stage or other analysis stage). These shorter parts can be archived in some examples. For instance, a portion of the continuous substrate including a sample of a particular patient can be cut from the continuous substrate film 1 (e.g., for archiving purposes).

A sample applicator 2 is arranged downstream of the supply roll 9 and is configured to apply a single trace of a biological sample onto the continuous substrate film 1 being moved below it by the film transportation device 20. In one example, the sample applicator 2 can be coupled to a height adjustment device 6, which is configured to change a height of the sample applicator 2 over a surface of the continuous substrate film 1. The height adjustment can happen continuously during the application of the trace of a biological sample. In other examples, the height adjustment can happen at predetermined points in time and/or before an application of a trace of biological material starts. Examples of heights of the sample applicator that can be advantageous in some situations will be discussed below.

In some examples, the height adjustment device 6 of each applicator can be configured to move the sample applicator 2 only among a straight trajectory to vary a height of said applicator over the continuous substrate film 1. For instance, the straight trajectory can be parallel to a surface normal of the continuous substrate film 1, or can enclose an angle with the surface normal of the continuous substrate film 1.

In the example of FIG. 1, the trajectory of the movement of the applicator 2 is perpendicular to the surface of the continuous substrate film 1. However, the applicator 2 can also approach the film 1 along a tilted trajectory in some example to change the height of the applicator 2 over a surface of the continuous substrate film 1.

The above discussed only refers to movement taking place as part of the trace application process. It can be possible to move the sample applicator 2, e.g., as part of an installation or calibration process.

The sample applicator 2 being only movable along one direction (or in two directions) can make the application process of the trace of biological material comparatively simple. Only the height over the sample (the z-direction) has to be precisely controlled during the application process. The position of the sample applicator 2 in the other two spatial directions (x-direction and y-direction) can remain fixed in some examples.

In alternative examples, the sample applicator 2 can be completely stationary during the deposition process (i.e., without the height adjustment capability shown in FIG. 1). In still other examples, the sample applicator 2 can be configured to move in a direction orthogonal to the transport direction over a broad surface of the continuous substrate film 1 (the y-direction) (i.e., in order to apply the biological sample in a serpentine or zig-zag trace). While this might require additional components to move the sample applicator 2 in the y-direction, it can be possible to apply a two-dimensional trace in these examples. However, the sample applicator 2 is not configured to move in the transport direction of the continuous substrate film 1. This movement is provided by the transportation device 20.

The apparatus 25 can include a detector for measuring a height of the sample applicator 2 (e.g., an applicator tip of the sample applicator). This measured height can be used to adjust a height of the sample applicator 2 to a particular height (or to a particular range of heights) during the trace application process. Example height ranges are discussed below.

In one example, the detector for measuring the height uses a direct image of the sample applicator 2 and a reflected image of the sample applicator 2 to determine a height of the sample applicator 2 over the surface of the continuous substrate film 1. For instance, a height detection method can include obtaining an image of the sample applicator 2 over the continuous substrate film 1, the image comprising a direct image region corresponding to the sample applicator 2 and a first reflected image region corresponding to an image of the sample applicator 2 reflected from a surface of the continuous substrate film 1, determining a position of an edge of the sample applicator 2 in the direct image region, determining a position of a reflected edge of the sample applicator 2 in the first reflected image region, determining a distance between the edge of the sample applicator 2 and the reflected edge of the sample applicator 2 and determining the position of the sample applicator 2 relative to the continuous substrate film 1 based on the distance between the edges.

In other examples, the detector for measuring the height uses a reflected image of the sample applicator 2 from an upper surface of the continuous substrate film 1 and possibly also a reflected image from a lower surface of the continuous substrate film 1 to determine a height of the sample applicator 2 over the surface of the continuous substrate film 1. For instance, measuring a height of the sample applicator 2 over the continuous substrate film 1 can include obtaining an image of a particular sample applicator 2 over the continuous substrate film 1, the image comprising a first image region corresponding to the sample reflected from a first surface of the continuous substrate film 1 and a second image region corresponding to the sample reflected from a second surface of the continuous substrate film 1, determining a position of a reflected edge of the sample applicator 2 in the first reflected image region, determining a position of a reflected edge of the sample applicator 2 in the second reflected image region, determining a distance between the reflected edges of the sample applicator 2 in the first and second reflected image regions and determining the position of the sample applicator 2 relative to the continuous substrate film 1 based on the distance between the edges.

In the example of FIG. 1, an applicator tip of the sample applicator 2 is held at a distance from the continuous substrate film 1 during the sample application process. In other examples, the applicator tip can come into contact with a surface of the continuous substrate film 1 during the application process. In these situations, the applicator unit 26 can be configured to vary the force of the application process of the biological sample onto the continuous substrate film 1 to control the application process. Such apparatus can include a force adjustment device, which can be configured and operate similarly as the height adjustment device 6 discussed above.

The transportation device 20 of FIG. 1 can include an optional application stage support roller 4 that supports the continuous substrate film 1 in an area where the sample applicator 2 is located. This can improve a positional stability of the continuous substrate film 1 in the area of the sample applicator 2. In particular, a positional stability in the z-direction can be improved in some examples.

The transportation device 20 can move the continuous substrate film 1 continuously during the application process. In other examples, the transportation device 20 is configured to move the continuous substrate film 1 intermittently during the application process. In the same manner, the sample applicator 2 can apply the sample continuously or intermittently (e.g., the sample applicator 2 can be configured to apply a series of dots of the biological sample onto the surface of the continuous substrate film 1).

After the trace of the biological sample has been applied to the continuous substrate film 1, the transportation device 20 can move the continuous substrate film 1 further downstream. The apparatus 25 of FIG. 1 includes an imaging stage 3 located downstream of the sample applicator 2.

In other examples, the apparatus 25 can include another analyzer for analyzing the trace of the biological sample than an imaging stage. Examples of properties to be analyzed have been listed above. For example, the apparatus 25 can include a non-imaging optical sensor configured to determine an optical property of the trace of the biological sample (e.g., one or more of a diffuse or direct transmission property of the trace, a diffuse or specular reflection property of the trace, an absorption property of the trace or a fluorescence property of the trace). In still other examples, the analyzer can include a sensor other than an optical sensor (e.g., a tactile sensor, a conduction sensor, a magnetic field sensor or a chemical sensor). In general, the apparatus 25 can be equipped with a suitable sensor to detect any desired chemical, biological, or physical property of the trace of the biological sample.

The imaging stage 3 can include one or more cameras attached to an imaging optics to take images of the trace of biological sample. In one example, the imaging optics includes one or more microscope objectives (e.g., a microscope providing a magnification of 20× or higher). The images taken by the imaging stage 3 can be further processed in an analyzer of an analysis system (e.g., in order to determine one of the parameters discussed above).

In one example, the imaging stage 3 can be coupled to a height adjustment device 17, which is configured to change a height of the imaging stage 3 over a surface of the continuous substrate film 1. The height adjustment can happen continuously during the application of the trace of a biological sample. In other examples, the height adjustment can happen at predetermined points in time and/or before an application of a trace of biological material starts.

In some examples, the imaging stage 3 is not configured to move in another direction than in a direction perpendicular to the surface of the continuous substrate film 1 when the film is present in the apparatus 25 (i.e., to adjust the height of the imaging stage 3). This only refers to movement taking place as part of the trace application process. It can be possible to move the imaging stage 3, e.g., as part of an installation or calibration process.

The transportation device 20 of FIG. 1 includes an optional imaging stage support roller 5 that supports the continuous substrate film 1 in an area where the imaging stage 3 is located. This can improve a positional stability of the continuous substrate film 1 in the area of the imaging stage 3. In particular, a positional stability in the z-direction can be improved in some examples.

As shown in FIG. 1, the apparatus 25 for preparing a biological sample for analysis according to an embodiment of the present disclosure can include several additional optional components.

On the one hand, the apparatus 25 of FIG. 1 can include an indexing stage 16, which is configured to apply index markers to indicate a position on the continuous substrate film 1. In one example, the indexing stage 16 includes one or more optical devices (e.g., laser devices) adapted to mark the continuous substrate film 1. The indexing stage 16 can receive information regarding a transport speed of the continuous substrate film 1 and mark the continuous substrate film 1 in response to the transport speed information.

The index markers can be used in determining a position on the continuous substrate film 1 in images of the imaging stage 3. In other examples, the continuous substrate film 1 can have pre-applied index markers indicating a position on the continuous substrate film 1 (that can make an indexing stage superfluous). In still other examples, index markers can be physically applied to the film as it passes (e.g., by as using an inkjet printer head).

Moreover, the apparatus of FIG. 1 can include an optional substance application stage 8 configured to apply one or more substances onto the trace of the biological sample in order to treat the sample in some predetermined fashion, e.g., to rinse, fix, stain or protect the biological sample). In one example, the substance application stage 8 can include a printer configured to print the substance onto the trace of a biological sample. In other examples, the substance application stage 8 can include a sprayer configured to spray the substance onto the trace of a biological sample. The optional substance application stage 8 can be configured to apply a staining agent onto the trace of the biological sample. In one example, the biological sample includes cells that can be stained by the staining agent.

Examples of stains that can be employed in the substance application stage 8 may include: Wright-Giemsa stain, Geimsa stains, and Romanowsky stains. Other solutions that could be dispensed are fixatives (e.g., methanol) and buffer solutions. Other visualization methods involving immunocytochemical reagents or other markers of specific cell components may also be used.

In other examples, the substance application stage 8 can be combined with the sample applicator 2. For instance, the substance application stage 8 can be integrated into the sample applicator 2. In one example, the sample applicator 2 includes an integrated staining agent application stage. The staining agent can be mixed with the biological sample before application in some examples. Examples of staining agents that can be used in this example may include: Romanowsky stains, reticulocyte stains, and stains using specific antibodies. Additional stains may be used in the apparatus of the present disclosure including hematoxylin and eosin; immunocytochemical stains; histochemical stains for viewing cellular components; and antibody, aptamer or other stains based on binding a ligand to an antigen.

In other examples, the substance application stage 8 can be configured to apply a different agent than a staining agent onto the trace of the biological sample. In still other examples, the substance application stage 8 can be configured to apply a protecting substance that can form a protective cover over the trace of the biological sample.

Various fixatives and diluents may be used with the substance application stage 8 (or a substance application stage integrated into the sample applicator 2 as described above). For example, 85% methanol can be used as the fixative. For some staining agents an ethyl alcohol or formaldehyde based fixative can be used. Diluents useful for diluting whole blood, for example, may include salt solutions or protein solutions. Salt solutions range from "physiological saline" (0.9 N), to complex mixtures of salts, to the commercial preparation PLASMALYTE® that simulates virtually all the salts found in human blood serum. Protein solutions can range from simple solutions of bovine albumin to PLASMANATE®, a commercial preparation with selected human plasma proteins. Such preparations can vary in protein concentrations, buffers, pH, osmolarity, osmalality, buffering capacity, and additives of various types. Synthetic or "substitute" versions of these solutions may also be usable, including FICOLL® or Dextran or other polysaccharides. Other substitutes may be used. An example of a diluent is PLASMALYTE® plus PLASMANATE® in the proportion of 4:1 (PLASMALYTE®:PLASMANATE®). Another example of a diluent is 5% albumin. When analyzing whole blood, a dilution of 2 parts blood to 1 part diluent can be used, where the diluent is a physiologically compatible solution, but a range of dilution from 0:1 (no dilution) to 10:1 (diluent:blood) may be used in alternate examples.

Moreover, the apparatus 25 of FIG. 1 includes an optional dryer 7 that is located downstream of the sample applicator 2 (and optionally of the substance application stage 8). The drier 7 is configured to dry the trace of the biological sample on the continuous substrate film. The drying can include using one or more of the following principles for the drying process: exposing the substrate film 1 to an air movement, exposing the substrate film 1 to warmed air, exposing the substrate film to dried air, and/or exposing the substrate film 1 to heat radiation.

In addition, the imaging stage 3 of the apparatus 25 for preparing a biological sample for analysis can include an optional illumination stage (not shown in FIG. 1) configured to illuminate an area of the continuous substrate film 1 that is imaged. In one example, the illumination stage can include a light source configured to illuminate the continuous substrate film 1 with light including two or more different wavelength bands. For instance, the illumination stage can include a plurality of LED light sources configured to emit light in different wavelength bands. For example, a first wavelength band of the plurality of wavelength bands can range from 380 nm to 450 nm ("blue"), a second wavelength band can range from 450 nm to 580 nm ("green") and a third wavelength band can extend from 580 nm to 820 nm ("red"). The illumination stage can also include UV light sources (i.e., having an emission wavelength below 350 nm) or IR light sources (i.e., having an emission wavelength above 820 nm).

After several components of an apparatus for preparing a biological sample for analysis according to the present disclosure have been discussed in connection with FIG. 2, different properties of the trace of biological material and the sample applicator will subsequently be treated in more detail in connection with FIG. 2.

Figure 2:
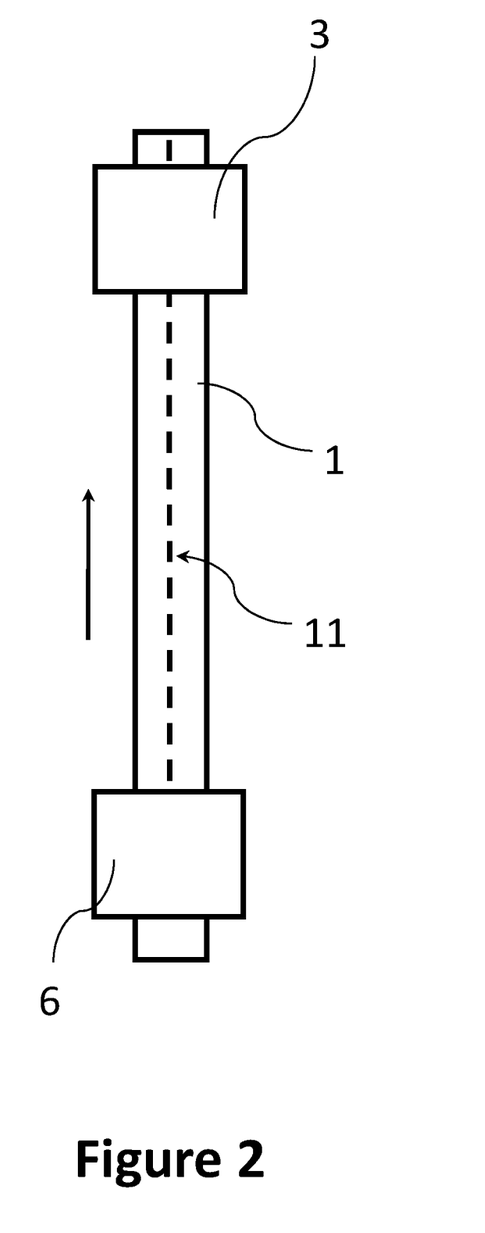
FIG. 2 illustrates an example continuous substrate film onto which a trace of biological material has been applied according to an embodiment of the present disclosure.

FIG. 2 depicts a view from above onto a continuous substrate film 1 onto which a trace of a biological sample 11 is applied by a sample applicator 2 (see, e.g., FIG. 1). The continuous substrate film 1 with the trace of the biological sample 11 is subsequently transported towards an imaging stage 3 (or another analyzer).

In certain embodiments, the sample applicator 2 includes an applicator tip for ejecting the biological sample 11 onto the continuous substrate film 1.

The applicator 2 may comprise a syringe, a manual or motor driven pipettor or a motor controlled pump attached through a tube to the applicator tip. The pump may be a peristaltic pump, a syringe pump, or other similar device (in one example that allows small volumes of fluid samples containing cells to be aspirated and dispensed through an orifice). In still other examples, the sample can be applied by electrostatic expulsion from an orifice.

In some examples, an orifice will be contained in the applicator tip that is two to five millimeters in outside diameter with an inner diameter of between 0.1 and 1 millimeters (e.g., between 0.4 and 0.6 mm).

In another example, the sample applicator tip can have an outer diameter of about 1500 to 500 microns and an inner diameter of about 500 to 100 microns e.g., a sample applicator with an outer diameter of about 812 microns and an inner diameter of about 431 microns). This sample applicator tip can be controlled to maintain above the surface of the continuous substrate film 1 in a height of between 8 to 20 microns (e.g., 10, 12, 14, 16, or 18 microns). On average, for example, the height of the sample applicator tip above the surface of the continuous substrate film 1 can be maintained at about 12 microns. At this height, it can be ensured that rows of blood are dispensed with sufficient uniformity in some examples. A height of the sample applicator tip above the substrate can be kept constant within 2 microns in some examples.

The applicator tip may be disposable or washable. The applicator tip may be rounded to facilitate insertion and cleaning of the tip. Fluid flow through the tip is controlled to allow a thin layer (e.g., substantially a monolayer) of a biological sample (e.g., containing cells) to be deposited onto the continuous substrate film 1.

By optimizing flow rate through the tip and the relative speed (e.g., a speed with which the transportation device moves the continuous substrate film 2 under the sample applicator 2) and height of the tip over the continuous substrate film 1, an appropriate density of cells can be deposited onto the continuous substrate film 1.

In one embodiment, the flow rate through the applicator tip is between 0.01 and 1 microliter per second (e.g., between 0.05 and 0.15 microliters per second) while the continuous substrate film 1 is moving at a speed of between 1 and 100 millimeters per second (e.g., between 20 and 40 millimeters per second) under the applicator tip at a height of between 20 microns and 120 microns (e.g., between 50 and 90 microns).

In another embodiment, for example when the body fluid comprises undiluted blood, the flow rate through the tip is between 0.005 and 0.2 microliters per second (e.g., between 0.01 and 0.1 microliters per second) while the continuous substrate film 1 is moving at a speed under the applicator tip at a speed of between 10 and 120 millimeters per second (e.g., between 30 and 70 millimeters per second) at a height of between 2 and 20 microns (e.g., between 5 and 15 microns) above the surface of the continuous substrate film 1. The viscosity and consistency of the particular body fluid specimen will influence the flow rate through the tip and the relative speed and height of the tip over the continuous substrate film 1 required to ensure that an appropriate density of cells are deposited on the continuous substrate film 1 for examination.

In use, the sample applicator unit 26 may comprise a known volume of body fluid such as between 1 and 50 microliters (e.g., between 20 and 40 microliters). Some body fluids may be pre-processed to disperse cells that may be clumped together or to minimize mucous or other protein material that may cause the cells to stick together. Other body fluids such as urine may be concentrated before the body fluid is placed into the sample applicator unit 26.

The sample applicator unit 26 may mix this fluid with a stain or diluent, and eject a portion of this fluid onto the continuous substrate film 1 to form trace 11. A typical sub-sample would be an aliquot of approximately ½ μl to 2 μl but may be in the range of ⅒ to 10 μl.

In some embodiments, the apparatus 25 for preparing a biological sample for analysis according to the present disclosure or the sample applicator 2 may contain a first reservoir for storing the body fluid and a second reservoir for storing diluent. In some embodiments the body fluid will not be diluted.

The sample applicator unit 26 may comprise a hydraulic piston for pushing the fluid out of a fluid chamber (e.g., a syringe or a pipette). An applicator tip may be provided for adjusting the flow rate of the fluid. While size of the tip might not affect the speed (ul/sec) in which the solution flows out of the tip, generally, the smaller the opening in the tip, the greater the force generated by the fluid flowing from the tip. Additionally, the size of the tip affects thickness of the fluid flows. A tip having, i.e., a 0.3 millimeter inner diameter may provide for a flow rate of 0.1 microliters per second, and a width of the trace 11 may be 500 microns. The apparatus 25 may be configured to account for variances in the number of cells in a given body fluid specimen.

In general, a width of the trace 11 can be lower than 2 mm (e.g., lower than 1 mm). A width of the trace 11 can be determined by a geometry and operating conditions of the sample applicator 2 as well as by properties of the biological sample applied (e.g., a viscosity of the biological sample).

A number of cells placed on the continuous substrate film 1 using this method will vary depending on the type of body fluid being examined and the dilution ratio.

In some examples, a computer may control the speed at which the continuous substrate film 1 moves under the sample applicator 2, which could affect the thickness of the fluid resting on the continuous substrate film 1. The trace 11 can be continuous or intermittent.

The continuous substrate film 1 can be configured in various different ways. In general, as described above, the continuous substrate film 1 is much longer than wide (e.g., more than 20 times as long) and relatively thin (e.g., thinner than 2 mm). In one example, the continuous substrate film 1 can be more than 5 m long (e.g., more than 20 m or more than 100 m long). In addition or alternatively, the continuous substrate film 1 can be less than 10 cm wide (e.g., less than 5 cm or less than 1 cm wide). However, in other examples the continuous substrate film 1 can be more than 10 cm (e.g., more than 20 cm).

In the example of FIG. 2, the trace 11 of the biological sample is (substantially) linear. In other examples, the trace 11 of the biological sample can have a two-dimensional shape. For instance, the trace 11 of the biological sample can include curved segments or linear segments extending in different directions (e.g., the trace 11 of the biological sample can be a zig-zag trace or a serpentine trace). The sample applicator unit 26 of the present disclosure can be controlled to deposit a trace 11 of the biological sample, which can include curved segments or linear segments extending in different directions. For example, the sample applicators 2 can be configured to move in a direction orthogonal to the transport direction of the continuous substrate film 1. In this case, a combined movement of the continuous substrate film 1 (e.g., in the x-direction) and the sample applicator 2 (in the y-direction) can result in an application of the trace 11 of the biological sample in a non-linear pattern.

In still other examples, the apparatus 25 of the present disclosure can be configured to apply an intermittent trace of the biological sample (e.g., a trace including discrete strips or spots).

The continuous substrate film 1 can be provided in form of a film roll configured to be inserted in the apparatus 25 for preparing a biological sample for analysis. In some examples, the continuous substrate film 1 can be provided continuously from a film roll over a predetermined period of time for the sample preparation and analysis process (e.g., a film roll can provide the continuous substrate film 1 for one hour or more or five hours or more of sample preparation and analysis).

In examples where the biological sample to be applied includes cells, the trace 11 of the biological sample can form substantially a monolayer of cells on a surface of the continuous substrate film 1.

Several aspects of the continuous substrate films 1 configured to receive a trace 11 of a biological sample for analysis that can be used in the methods and apparatus of the present disclosure will be discussed in the next sections.

The continuous substrate film 1 can include (or consist of) one or more plastic materials. In one example, the continuous substrate film 1 can include two or more layers of the same or different materials (e.g., two or more layers of a plastic material). One plastic material that can be used is polyphtalate polycarbonate. In some examples a surface of the continuous substrate film 1 onto which the trace 11 of the biological sample is applied includes (or consists of) a polyphthalate polycarbonate.

In other examples, a surface of the continuous substrate film 1 onto which the trace 11 of the biological sample is applied includes (or consists of) a polyvinyl chloride. In still other examples, a surface of the continuous substrate film 1 onto which the trace 11 of the biological sample is applied includes (or consists of) a polyvinyl chloride.

In still other examples a surface of the continuous substrate film 1 onto which the trace 11 of the biological sample is applied or the complete continuous substrate film 1 includes (or consists of) a polyester (PES), a polyethylene terephthalate (PET), a polyethylene (PE), a high-density polyethylene (HDPE), a polyvinylidene chloride (PVDC), a low-density polyethylene (LDPE), a polypropylene (PP), a polystyrene (PS), a high impact polystyrene (HIPS), a polyimide. (PA) or a polyurethane (PU).

In other examples, the continuous substrate film 1 can include (or consist of) a metal material (e.g., aluminum or one of its alloys or iron or one of its alloys).

The surface of the continuous substrate foil onto which the trace(s) 11 of a biological sample are to be applied can be coated or functionalized. In one example, a coating is applied to a surface of the continuous substrate film 1 onto which the trace 11 of a biological sample for analysis is to be deposited, which improves adherence of the trace 11 of the biological sample. In one example, the surface of the continuous substrate film 1 onto which the trace(s) 11 of a biological sample are to be applied is treated to make the surface more hydrophilic, more hydrophobic, or even combinations of both in particular patterns. For example, in order to retain hydrophilic stains over the section of the film 1 to which a biological sample has been applied, the area where the sample is deposited can be made more hydrophilic to enhance retention of the stain near the sample, while other portions of the film 1 can be made hydrophilic to repel the stain toward the region where the sample is deposited and perhaps prevent the stain from spilling over the sides of the film 1 and into the instrument. In other examples, the surface of the continuous substrate film 1 onto which the trace(s) 11 of a biological sample are to be applied has a surface that includes a fixation agent for the biological sample.

A thickness of the continuous substrate film 1 can be at most 2-500 μm, typically between 50-200 μm.

After multiple aspects of an apparatus 25 for preparing a biological sample for analysis according to the present disclosure have been discussed in connection with FIG. 1 and FIG. 2, variants of the apparatus 25 for preparing a biological sample for analysis according to the present disclosure will be discussed subsequently in connection with FIG. 3 and FIG. 4.

Figure 3:
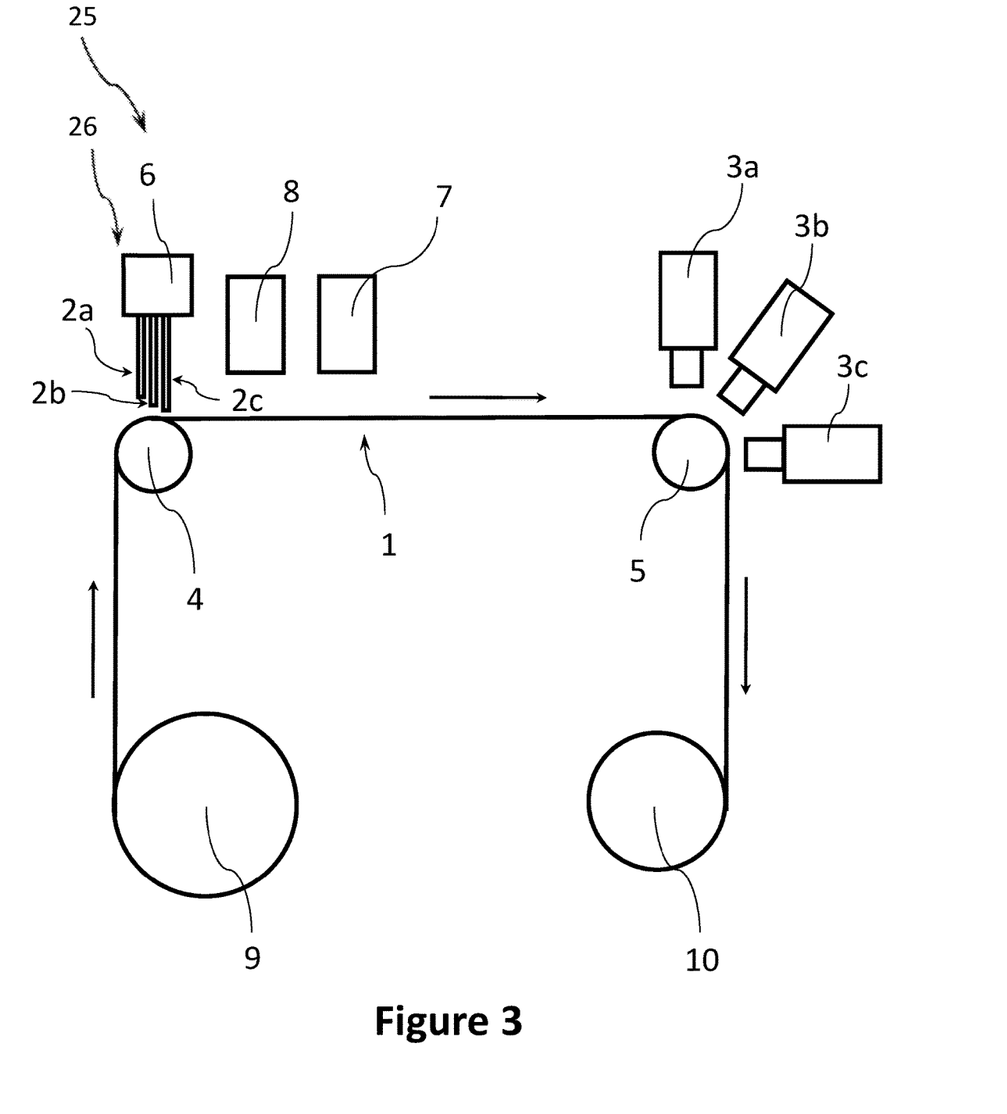
FIG. 3 illustrates another example apparatus for preparing a biological sample for analysis according to an embodiment of the present disclosure.

As can be seen in FIG. 3, the apparatus 25 for preparing a biological sample for analysis according to the present disclosure includes multiple sample applicators 2a, 2b, 2c and multiple imaging stages 3a, 3b, 3c.

The multiple sample applicators 2a, 2b, 2c (e.g., two, three or more than three sample applicators) can be configured to apply multiple traces 11 of a biological sample. In one example, the multiple sample applicators 2a, 2b, 2c can be configured to apply a plurality of parallel traces 11 of a biological sample onto h continuous substrate film 1. An example in which the sample applicators deposit three parallel traces 11a, 11b, 11c is depicted in FIG. 4.

The multiple sample applicators 2a, 2b, 2c have a single height adjustment device 6, which is configured to change a height of the multiple sample applicators 2a, 2b, 2c over a surface of the continuous substrate film 1 simultaneously. In other examples, each sample applicator can have a dedicated height adjustment device to adjust the respective sample applicator's height over a surface of the continuous substrate film 1 independently from the height of the other sample applicators.

Each of the sample applicators 2a, 2b, 2c can be configured as described in connection with the single sample applicator 2 in FIG. 1 and FIG. 2. For example, each of the sample applicators 2a, 2b, 2c can include a biological sample reservoir, a pumping device configured to force the biological sample out of the biological sample reservoir and an applicator tip configured to apply a trace 11 of the biological sample onto the continuous substrate film 1. In other examples, the two or more sample applicators can have a common biological sample reservoir and separate pumping devices and applicator tips. In still other examples, the two or more sample applicators can have a common reservoir for the biological sample and a common pumping device but separate applicator tips.

Figure 4:
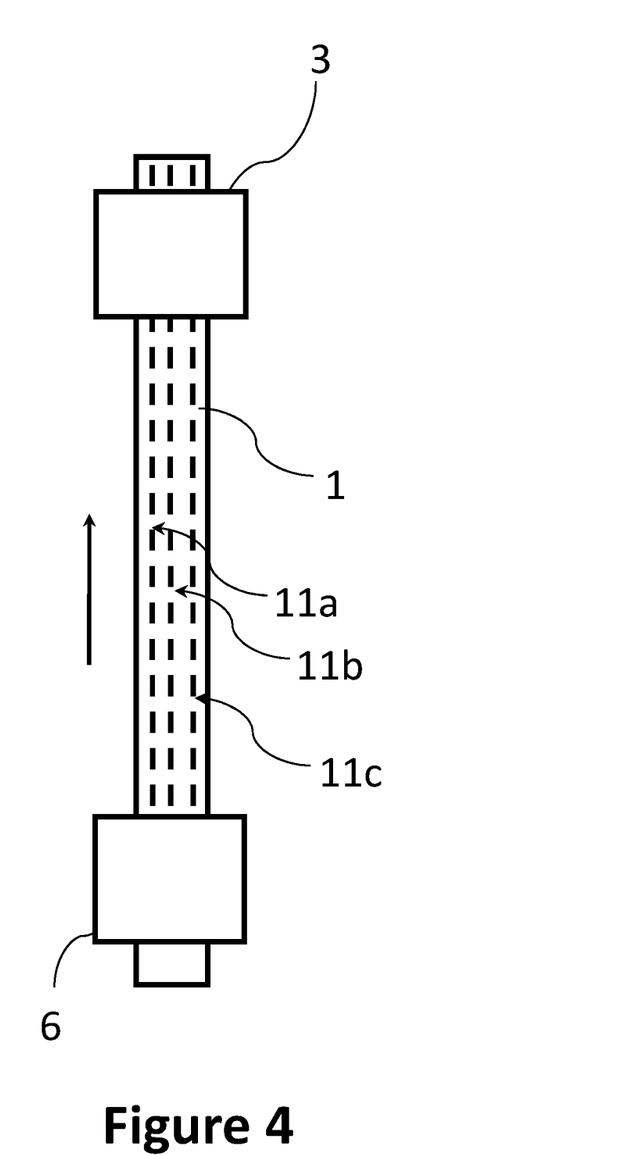
FIG. 4 illustrates an example continuous substrate film onto which a trace of biological material has been applied according to an embodiment of the present disclosure with an apparatus of FIG. 3.

Even though the multiple sample applicators 2a, 2b, 2c in FIG. 3 and FIG. 4 are configured to apply parallel traces, in other examples multiple sample applicators are configured to apply traces that partly or completely overlap. For instance, two or more sample applicator tips can be arranged offset only in a transfer direction of the continuous substrate film 1. These sample applicators can be configured to apply two or more traces that (at least partially) overlap. In one example, a second sample applicator can be configured to apply a second trace of a biological sample on top of a first trace of a biological sample applied by a first sample applicator. In other examples, two or more of the sample applicators can be configured to apply intermittent traces of a biological sample that form a trace of the biological sample in combination.

In general, the apparatus 25 for preparing a biological sample for analysis according to the present disclosure can include a number of sample applicators arranged in a two-dimensional pattern over the continuous substrate film 1 (i.e., the sample applicators are offset in the x-direction and/or in the y-direction as defined above). For instance, the sample applicators can be arranged in a line-shaped or rectangular-shaped pattern.

In some examples, the two or more traces can form a closed film of sample material on the surface of the continuous substrate 1. In examples where the biological sample to be applied includes cells, the closed film of the biological sample can form substantially a monolayer of cells on a surface of the continuous substrate film 1.

In an apparatus 25 for preparing a biological sample for analysis according to the present disclosure including multiple sample applicators, each of the multiple sample applicators can be configured to apply the same biological sample. However, in other examples, two or more of the sample applicators can be configured to apply different biological samples. For instance, a first trace can be sampled from a first biological sample belonging to a first patient while a second trace can be sampled from a second biological sample belonging to a second patient. In other examples, a first trace can be sampled from a biological sample of a first type while a second trace can be sampled from a biological sample of a second type. In further examples, a first trace can be made with a first biological sample belonging to a first patient and a second trace can be made with a quality control material, such as a standardized suspension of cells of known types.

Each of the different traces of the sample applicators 2a, 2b, 2c can be imaged by a separate imaging stage 3a, 3b, 3c. In other examples, a single imaging stage (e.g., a camera with a single microscope objective) can be used to image more than one or all traces on a continuous substrate film 1.

In other examples of the apparatus 25 for preparing a biological sample for analysis according to the present disclosure, two or more continuous substrate films are handled in parallel. For instance, an apparatus 25 for preparing a biological sample for analysis according to the present disclosure can include two or more sets of the components described in connection with FIG. 1 or FIG. 3. In one example, two or more continuous substrate films 1 are moved below an arrangement of multiple sample applicators 2a, 2b, 2c as described in connection with FIG. 3 above. For instance, the two or more continuous substrate films 1 can be arranged to move in parallel below a sample applicator.

In the same manner, a single imaging stage (e.g., a camera having a microscope objective) can be configured to image traces of biological sample material on two or more continuous substrate films in parallel. In other examples, different imaging stages can be arranged to image traces on different continuous substrate films.

After two different configurations of an apparatus 25 for preparing a biological sample for analysis according to the present disclosure have been discussed in connection with FIG. 1 to FIG. 4, a third variant will be subsequently discussed in connection with FIG. 5. Even though the apparatus 25 of FIG. 1, FIG. 3 and FIG. 5 are presented as different examples, the components of the apparatus 25 of the different figures can also be combined.

Figure 5:
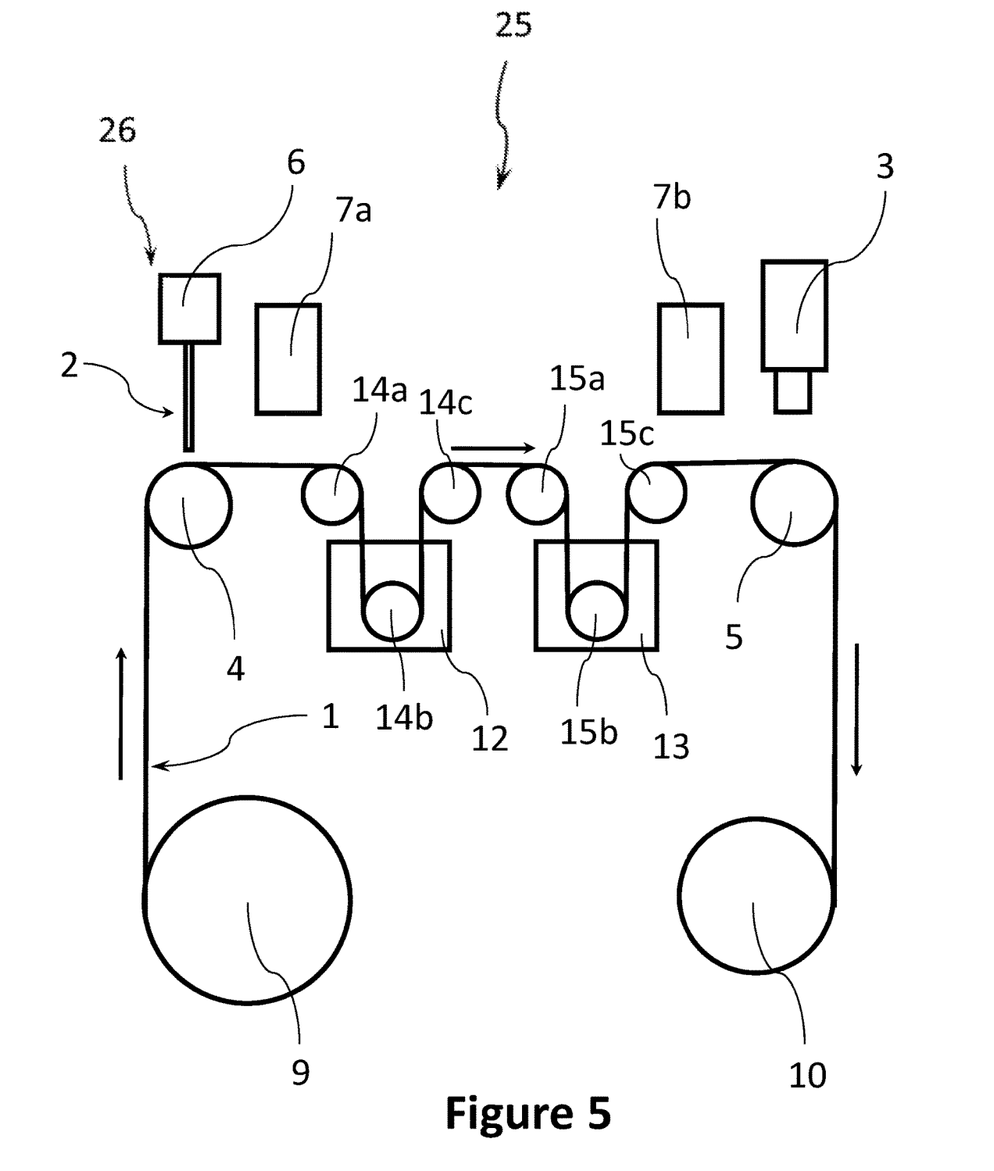
FIG. 5 illustrates yet another example apparatus for preparing a biological sample for analysis according to an embodiment of the present disclosure.

As can be seen in FIG. 5, the sample applicator unit 26 and the imaging stage 3 are arranged in a similar manner as in the apparatus 25 of FIG. 1.

However, the apparatus 25 of FIG. 5 includes an alternative configuration of a substance application stage. The apparatus of FIG. 5 includes two substance application stages 12, 13 in the form of baths through which the continuous substrate film 1 is guided. In one example, a first bath substance application stage 12 can apply a fixation agent to the continuous substrate film 1 to fixate the trace of the biological samples. In addition or alternatively, a second bath substance application stage 13 can apply a staining agent to the continuous substrate film 1 to stain one or more constituents of the trace of the biological samples.

In other examples, the apparatus 25 can include additional bath substance application stages or only one bath substance application stage (e.g., to apply one or more staining agent(s) or fixation agent(s)). The bath substance application stages can apply to the continuous substrate film 1 any substance discussed above in connection with FIG. 1 or FIG. 2.

Moreover, the apparatus 25 of FIG. 5 can include two dryers 7a, 7b arranged upstream and downstream of the bath substance application stages 12, 13. The first dryer 7a upstream of the bath substance application stages 12, 13 can be configured to dry the trace of the biological sample after the biological sample has been applied by the sample applicator 2. The second dryer 7b downstream of the bath substance application stages 12, 13 can be configured to dry the trace of the biological sample after the one or more substances have been applied to the continuous substrate film 1.

The apparatus 25 of FIG. 5 can also include several deflection rollers 14a-14c, 15a-15c arranged to steer the continuous substrate film 1 through the bath substance application stages 12, 13.

As can be seen in FIG. 5, the continuous substrate film 1 is deflected by the deflection rollers 14a-14c, 15a-15c by an angle of approximately 90°. In other examples, the deflection angle can be different.

Furthermore, in some examples the continuous substrate film 1 is not substantially deflected between the sample applicator 2 and the imaging stage 3 (e.g., an aggregate angle of deflection of the continuous substrate film 1 is lower than 20° between the sample applicator 2 and the imaging stage 3). This can be helpful to avoid delamination of the trace 11 from the continuous substrate film 1.

In connection with FIG. 1 to FIG. 5 above, different apparatus 25 for preparing a biological sample for analysis according to the present disclosure have been discussed. Each of these apparatus 25 for preparing a biological sample can include one or more computer systems to control the above described operations of the apparatus 25 for preparing a biological sample.

The one or more computer systems may include a laptop as shown, or a server, workstation, or any other type of computing device. The one or more computer systems may comprise a processor, a display, an interface, and internal memory and/or a disk drive. The one or more computer systems may also comprise software stored in the memory or on computer readable media such as an optical drive. The software may comprise instructions for causing the one or more computer systems to operate the sample applicators 2, 2a, 2b, 2c, the continuous substrate transportation device 20, the imaging stages 3, 3a, 3b, 3c, the indexing stage 16, the one or more substance application stage 8, or any component connected to one of these components or included in the apparatus 25 for preparing a biological sample.

Similarly, the one or more computer systems may receive information from any of these components. For example, the software may control the speed of the continuous substrate film 1. In addition, the one or more computer systems may also be responsible for performing the analysis of the images captured by the imaging stage(s).

In a particular example capable of preparing and analyzing cells from blood samples, the one or more computers may be able to calculate the number of a specific type of cell in a particular volume of blood, for example for blood, red cell, white cell, and platelet counts and other measured and derived components of the CBC such as: hemoglobin content, red blood cell morphology, or WBC differential could be calculated. The image analysis software may analyze each individual field and sum the total red and white cell counts. To calculate the total counts per microliter in the patient vial, the number counted on the continuous substrate film is multiplied by the dilution ratio and volume of the sub-sample. Results of the counts, morphologic measurements, and images of RBCs and WBCs from the continuous substrate film may be shown on a display of the one or more computer systems. In some embodiments, the one or more computer systems may be able to display numerical data, cell population histograms, scatterplots, and direct assessments of cellular morphology using images of blood cells displayed on the monitor. The ability to display cellular morphology provides users of the apparatus for preparing a biological sample, the ability to establish the presence or absence of abnormalities in cell morphology that may warrant preparing an additional trace of the biological sample for manual review by an experienced technician or other professional. The software may provide the one or more computers instructions to display images received from the one or more imaging stages or may cause the display to show the results (e.g., in a chart or graph) of an analysis of the images. Similarly, the one or more computer systems may be able to enumerate the number of cells of a specific type in a particular blood volume or enumerate the number of damaged cells, cancerous cells, or lysed cells in a particular volume of blood. The memory of the one or more computer systems may contain software to allow the one or more computer systems to perform the analysis process. The one or more computer systems may use one or more magnifications during the analysis. While the example above describes using an example of the disclosure for preparing and analyzing cells from a sample of blood, embodiments of the present disclosure may be used for preparing and analyzing cells from other fluids such as bone marrow, urine, vaginal tissue, epithelial tissue, tumors, semen, spittle, and/or other body fluids.

In some embodiments, the one or more computer systems may be linked together the one or more computer systems to share information. The one or more computer systems may also be connected to a network or laboratory information system to allow the computer to send and receive information to other computers.

The transportation device for the continuous substrate film can include one or more sensors to monitor a transport speed of the continuous substrate film. The one or more computer systems controlling the apparatus can receive a signal indicating a transport speed of the continuous substrate film and can control operations of one or more components in response to this signal (e.g., operations of a sample applicator or an imaging stage).

In addition or alternatively, the transportation device for the continuous substrate film can include one or more sensors to monitor a lateral position of the continuous substrate film. The one or more computer systems controlling the apparatus can receive a signal indicating a lateral position of the continuous substrate film and can control operations of one or more components in response to this signal e.g., operations of a sample applicator or an imaging stage or one or more actuators of the apparatus to adjust a lateral position of the continuous substrate film).

In the preceding detailed description multiple examples of methods for preparing a biological sample for analysis, apparatus for preparing biological samples for analysis and uses of continuous substrate films or preparing a biological sample for analysis of the present disclosure have been discussed. However, the analysis methods and systems of the present disclosure can also be configured as set out in the following aspects:

1. A method for preparing a biological sample for analysis, the method comprising:
   moving a continuous substrate film past a sample applicator unit including one or more applicators; and,
   applying at least one trace of a biological sample to be analyzed onto the continuous substrate film by the sample applicator unit.
2. The method of aspect 1 wherein the applicator unit includes one applicator or two or more applicators.
3. The method of aspect 1 or 2 further comprises moving each applicator of the applicator unit only in one direction or only in two directions.
4. The method of any of aspects 1 and 3 further comprising moving each sample applicator to vary the distance of said applicator to the continuous substrate film and/or to vary the force of the application process onto the continuous substrate film.
5. The method of aspect 4 wherein the sample applicators are stationary during the applying step expect for a movement to vary the distance of said applicator to the continuous substrate film and/or to vary the force of the application process onto the continuous substrate film.
6. The method of aspect 4 or 5 wherein each applicator moves only among a straight trajectory to vary the distance of said applicator to the continuous substrate film and/or or to vary the force of the application process onto the continuous substrate film.
7. The method of aspect 6 wherein the straight trajectory is parallel to a surface normal of the continuous substrate film or encloses an angle with the surface normal of the continuous substrate film.
8. The method of any one of aspects 1 to 7, wherein the moving the continuous substrate film includes moving the continuous substrate film in a roll-to-roll process.
9. The method of any one of aspects 1 to 8, wherein the moving the continuous substrate film includes supplying the continuous substrate film from a supply roll.
10. The method of aspect 9 further comprising receiving the continuous substrate film in a container after the at least one trace of a biological sample applied to the continuous substrate film has been analyzed.
11. The method of any of the preceding aspects further comprising cutting the continuous substrate film into a plurality of strips.
12. The method of any one of aspects 1 to 11 wherein the biological sample comprises a bodily fluid or a constituent thereof.
13. The method of aspect 12 wherein the bodily fluid is blood, bone marrow, urine, semen, saliva, gastric fluid, mucus, peritoneal fluid, cerebrospinal fluid, bile, or sweat, or a constituent of blood, bone marrow, urine, semen, saliva, gastric fluid, mucus, peritoneal fluid, cerebrospinal fluid, bile or sweat, or a constituent of these bodily fluids, or a concentrated or diluted form of said fluids.
14. The method of aspect 12 wherein the bodily fluid is blood or a constituent of blood.
15. The method of any one of the preceding aspects wherein the continuous substrate film includes a plastic material.
16. The method of any one of the preceding aspects wherein the continuous substrate film has a thickness of at most 2-500 µm, typically 50-200 µm.
17. The method of any one of the preceding aspects wherein each applicator includes an applicator tip configured to deposit the trace of the biological sample to be analyzed.
18. The method of aspect 17 wherein the applicator tip is a hollow needle configured to apply the biological sample onto the continuous substrate film.
19. The method of aspect 17 or 18 wherein the applicator tip has an outer diameter of two to five millimeters and an inner diameter of between 0.1 and 1 millimeters, typically between 0.4 and 0.6 mm.
20. The method of aspect 17 or 18 wherein the applicator tip has an outer diameter of between 500 and 1500 microns and an inner diameter of between 100 and 500 microns
21. The method of any one of the preceding aspects wherein the sample applicator unit is configured to apply two or more traces of the biological sample.
22. The method of aspect 21 wherein the sample applicator unit is configured to apply two or more parallel traces of the biological sample.
23. The method of any one of the preceding aspects, the method further comprising:
moving the continuous substrate film past a dryer to dry the trace of the biological sample after application, wherein the dryer typically uses one of the following principles for the drying process: exposing the substrate film to an air movement, exposing the substrate film to warmed air, exposing the substrate film to dried air, exposing the substrate film to heat radiation.
24. The method of any one of the preceding aspects further comprising adding an agent to the biological sample.
25. The method of aspect 24 wherein the agent is a staining agent.
26. The method of aspect 24 or aspect 25 wherein the staining agent is added after application of the trace of the biological sample.
27. The method of any of aspects 24 to 26 wherein adding the agent comprises spraying the agent onto the trace of the biological sample.
28. The method of any of aspects 24 to 26 wherein adding the agent comprises printing the agent onto the trace of the biological sample.
29. The method of any of aspects 24 to 26 wherein adding the agent comprises moving the continuous substrate film with the trace of the biological sample through a bath including the agent.
30. The method of any one of the preceding aspects wherein the trace of a biological sample has a substantially linear shape.
31. The method of any one of the preceding aspects further comprising moving the trace of the biological sample past an imaging stage to take one or more images of the trace of the biological sample.
32. The method of aspect 31 wherein the imaging stage includes one or more cameras and/or one or more microscope objectives.
33. The method of aspect 31 or aspect 32 wherein imaging stage is stationary over a surface of the continuous substrate film except for a movement in a direction perpendicular to a surface of the continuous substrate film.
34. The method of any one of the preceding aspects wherein the continuous substrate film includes index markers to indicate a position on the continuous substrate film.
35. The method of any one of the preceding aspects further comprising moving the continuous substrate film past an indexing stage to apply index markers to indicate a position on the continuous substrate film.
36. The method of aspect 35 wherein the indexing stage includes an optical indexer, typically a laser.
37. The method of any one of the preceding aspects wherein a direction of movement of the continuous substrate film does not change between the applicator and an imaging stage arranged downstream of the applicator.
38. The method of any one of the preceding aspects wherein the continuous substrate film is supported by a support in an area where the trace of the biological sample to be analyzed is applied onto the continuous substrate film by the each applicator.
39. The method of aspect 38 wherein the support includes a roller.
40. The method of any one of the preceding aspects wherein the continuous substrate film is supported by a support in an area where the trace of the biological sample to be analyzed is imaged by an imaging stage.
41. The method of aspect 40 wherein the support includes a roller.
42. The method of any one of the preceding aspects further comprising:
measuring a speed of movement of the continuous substrate film.
43. The method of aspect 42 further comprising:
using the measured speed of movement in a step of processing images of the trace of the biological sample.

44. The method of aspect 42 further comprising:
using the measured speed of movement to control movement of the continuous substrate film.
45. The method of any one of the preceding aspects further comprising measuring a height of each of the applicators over the continuous substrate film and controlling a height of each of the applicators over the continuous substrate film in response to the measurement.
46. The method of aspect 45 wherein measuring a height of each of the applicators over the continuous substrate film comprises:
obtaining an image of a particular sample applicator over the continuous substrate film, the image comprising a direct image region corresponding to the sample applicator and a first reflected image region corresponding to an image of the sample applicator reflected from a surface of the continuous substrate film;
determining a position of an edge of the sample applicator in the direct image region;
determining a position of a reflected edge of the sample applicator in the first reflected image region;
determining a distance between the edge of the sample applicator and the reflected edge of the sample applicator; and
determining the position of the sample applicator relative to the continuous substrate film based on the distance between the edges.
47. The method of aspect 45 or 46 wherein measuring a height of each of the applicators over the continuous substrate film comprise:
obtaining an image of a particular sample applicator over the continuous substrate film, the image comprising a first image region corresponding to the sample reflected from a first surface of the continuous substrate film and a second image region corresponding to the sample reflected from a second surface of the continuous substrate film;
determining a position of a reflected edge of the sample applicator in the first reflected image region;
determining a position of a reflected edge of the sample applicator in the second reflected image region;
determining a distance between the reflected edges of the sample applicator in the first and second reflected image regions; and
determining the position of the sample applicator relative to the continuous substrate film based on the distance between the edges.
48. The method of any one of the preceding aspects wherein the continuous substrate film is moved with a speed between 1 mm and 100 mm per second, typically between 20 mm per second and 70 mm per second.
49. The method of any one of the preceding aspects wherein the applicator is controlled to apply the biological sample at a rate of between 0.005 microliters per second and 1 microliter per second, typically between 0.05 microliters per second and 0.5 microliters per second.
50. The method of any one of the preceding aspects wherein an applicator tip is located at a height between 2 μm and 100 μm over a surface of the continuous substrate film during the application process, typically between 5 μm and 75 μm over a surface of the continuous substrate film.
51. The method of any one of the preceding aspects further comprising applying a protective film over the trace of the biological sample.
52. The method of aspect 51 wherein the protective film is applied by a wet coating process.
53. The method of aspect 51 wherein the protective film is laminated over the trace of the biological sample.
54. The method of any one of the preceding aspect wherein the biological sample includes cells and wherein the at least one trace of a biological sample forms substantially a monolayer of cells on a surface of the continuous substrate film.
55. An apparatus for preparing a biological sample for analysis, the apparatus comprising:
a film transportation device configured to move a continuous substrate film past a sample applicator unit; and,
the sample applicator unit including one or more applicators configured to apply a trace of a biological sample to be analyzed onto the continuous substrate film.
56. The apparatus of aspect 55, further comprising an imaging stage configured to take one or more images of the trace of the biological sample downstream of the applicator.
57. The apparatus of aspect 55 or 56, wherein the imaging stage includes one or more cameras and/or one or more microscope objectives.
58. The apparatus of any one of aspects 55 to 57 wherein the imaging stage includes an illumination stage configured to illuminate an area of the continuous substrate film which are imaged.
59. The apparatus of aspect 58 wherein the illumination stage includes one or more LED light sources configured to emit light in different wavelength bands.
60. The apparatus of any one of aspects 55 to 59 wherein the imaging stage is stationary with respect to a surface of the continuous substrate film except for a movement in a direction perpendicular to a surface of the continuous substrate film.
61. The apparatus of any one of the preceding aspects further comprising one or more agent applicators to apply an agent onto the trace of the biological sample.
62. The apparatus of aspect 61 wherein the one or more agent applicators include a bath, a spraying device and/or a printing device.
63. The apparatus of aspect 61 or aspect 62 wherein the agent is a staining agent.
64. The apparatus of any one of the preceding aspects further comprising an indexing stage to apply index markers to indicate a position on the continuous substrate film.
65. The apparatus of any one of the preceding aspects further comprising a supply roll arranged to supply the continuous substrate film and a waste film roll or a waste container arranged to receive the continuous substrate film after the trace of the biological sample has been analyzed.
66. The apparatus of any of the preceding aspects including one or more rollers to move the continuous substrate film.
67. The apparatus of any of the preceding aspects including one or more rollers to change a direction of movement of the continuous substrate film.
68. The apparatus of any one of the preceding aspects further comprising an application support in an area where the trace of the biological sample to be analyzed is applied onto the continuous substrate film by the sample applicator.
69. The apparatus of aspect 68 wherein the application support includes a roller.
70. The apparatus of any one of the preceding aspects further comprising an imaging support in an area where the trace of the biological sample to be analyzed is imaged.

71. The apparatus of aspect 70 wherein the imaging support includes a roller.
72. The apparatus of one of the preceding aspects further comprising a detector to determine a movement speed of the continuous substrate film.
73. The apparatus of any one of the preceding aspects wherein each applicator includes an applicator tip configured to deposit the trace of the biological sample to be analyzed.
74. The apparatus of aspect 73 wherein the applicator tip is a hollow needle configured to apply the biological sample onto the continuous substrate film.
75. The apparatus of aspect 73 or 74 wherein the applicator tip has an outer diameter of two to five millimeters and an inner diameter of between 0.1 and 1 millimeters, typically between 0.4 and 0.6 mm.
76. The apparatus of aspect 73 or 74 wherein the applicator tip has an outer diameter of between 500 and 1500 microns and an inner diameter of between 100 and 500 microns.
77. Use of a continuous substrate film in a process for preparing a biological sample for analysis, wherein the biological sample is applied as a trace of a biological sample onto the continuous substrate film by a sample applicator.
78. The use of aspect 77 wherein the continuous substrate film comprises a plastic material.
79. The use of any one of aspects 77 and 78 wherein the biological sample includes a bodily fluid.
80. The use of any one of aspects 77 to 79 wherein the bodily fluid is blood, bone marrow, urine, semen, saliva, gastric fluid, mucus, peritoneal fluid, cerebrospinal fluid, bile, or sweat, or a constituent of blood, bone marrow, urine, semen, saliva, or a constituent of these bodily fluids, or a concentrated or diluted from of said fluids.
81. A method for preparing a biological sample for analysis, the method comprising:
    moving a substrate past a sample applicator;
    applying a trace of a biological sample to be analyzed onto the substrate by the sample applicator, wherein the sample applicators are stationary during the applying step expect for a movement to vary the distance of said applicator to the continuous substrate film and/or to vary the force of the application process onto the continuous substrate film.
82. A method for preparing a biological sample for analysis, the method comprising:
    applying a trace of a biological sample to be analyzed onto the substrate by a sample applicator;
    moving the trace of the biological sample past an imaging stage to take one or more images of the trace of the biological sample, wherein the applicator moves only among a straight trajectory to vary the distance of said applicator to the continuous substrate film and/or or to vary the force of the application process onto the continuous substrate film.
83. A continuous substrate film configured to receive a trace of a biological sample for analysis, wherein the continuous substrate film includes a coating applied to a surface of the continuous substrate film onto which the trace of a biological sample for analysis is to be deposited to improve adherence of the trace of the biological sample.
84. The continuous substrate film of aspect 83 wherein the continuous substrate film further includes a reagent applied to a surface of the continuous substrate film onto which the trace of a biological sample for analysis is to be deposited
85. The continuous substrate film of aspect 83 wherein the reagent is adapted to be activated by adding water or a buffer solution.
86. The continuous substrate film of any one of aspects 83 to 85 wherein the continuous substrate film is transparent to light.
87. The continuous substrate film of any one of aspects 83 to 86 wherein the continuous substrate film has a thickness of at most 2-500 µm, typically 50-200 µm.
88. The continuous substrate film of any one of aspects 83 to 87 wherein the continuous substrate film is adapted to fixate blood or a constituent of blood, or a diluted or concentrated form of blood or a constituent of blood.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is noted that the terms "substantially" and "about" are utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. A method for preparing a biological sample for analysis, the method comprising:
   moving a continuous substrate film past a sample applicator unit including one or more sample applicators; and,
   applying, while moving the continuous substrate film, at least one trace of a biological sample to be analyzed onto the continuous substrate film by the sample applicator unit, wherein the biological sample includes cells and wherein the at least one trace of a biological sample forms substantially a monolayer of cells on a surface of the continuous substrate film.

2. The method of claim 1 wherein the applicator unit includes one sample applicator or two or more sample applicators.

3. The method of claim 1 further comprising moving each sample applicator to vary the distance between the applicator and the continuous substrate film, and/or to vary the force employed to apply the biological sample onto the continuous substrate film, wherein the sample applicators are stationary during the applying step, except for a movement to vary the distance between said applicator and the continuous substrate film, and/or to vary the force employed to apply the biological sample onto the continuous substrate film.

4. The method of claim 3 wherein each sample applicator moves only among a straight trajectory to vary the distance of said applicator to the continuous substrate film, and/or to vary the force of the application process onto the continuous substrate film.

5. The method of claim 1, wherein the moving the continuous substrate film includes supplying the continuous substrate film from a supply roll and receiving the continuous substrate film in a container or on a waste roll after the at least one trace of a biological sample applied to the continuous substrate film has been analyzed.

6. The method of claim 1, wherein the biological sample comprises a bodily fluid or a constituent thereof.

7. The method of claim 6, wherein the bodily fluid is blood or a constituent of blood.

8. The method of claim 1, wherein the sample applicator unit is configured to apply two or more traces of the biological sample.

9. The method of claim 1 further comprising adding a staining agent to the biological sample, wherein adding the staining agent comprises spraying the staining agent onto the trace of the biological sample, printing the staining agent onto the trace of the biological sample, or moving the continuous substrate film with the trace of the biological sample through a bath including the staining agent.

10. The method of claim 1 further comprising moving the trace of the biological sample past an imaging stage, wherein said imaging stage is configured to take one or more images of the trace of the biological sample.

11. The method of claim 10, wherein the imaging stage is stationary over a surface of the continuous substrate film except for a movement in a direction perpendicular to a surface of the continuous substrate film.

12. The method of claim 1, wherein the continuous substrate film is supported by a support in an area where the trace of the biological sample to be analyzed is applied onto the continuous substrate film by the one or more applicators, and/or wherein the continuous substrate film is supported by a support in an area where the trace of the biological sample to be analyzed is imaged by an imaging stage, wherein the support includes a roller.

13. The method of claim 1, wherein the sample applicator unit has a tip and said method comprises controlling the flow rate through the tip while applying the at least one trace of the biological sample onto the surface of the continuous substrate film.

14. The method of claim 1, further comprising controlling relative speed with which the transportation device moves the continuous substrate film under the sample applicator unit.

15. The method of claim 1, wherein the sample applicator unit has a tip and said method comprises controlling height of the tip over the continuous substrate film while applying the at least one trace of the biological sample onto the surface of the continuous substrate film.

16. The method of claim 1, wherein the sample applicator unit has a tip and said method comprises controlling the flow rate through the tip while applying the at least one trace of the biological sample onto the surface of the continuous substrate film, and wherein the flow rate through the tip is between 0.005 and 1 microliter per second.

17. The method of claim 1, wherein the sample applicator unit has a tip and said method comprises controlling relative speed with which the transportation device moves the continuous substrate film under the tip, and wherein the continuous substrate film is moving at a speed of between 1 and 120 millimeters per second under the tip.

18. The method of claim 1, wherein the sample applicator unit has a tip and said method comprises controlling height of the tip over the continuous substrate film while applying the at least one trace of the biological sample onto the surface of the continuous substrate film, and wherein the height is between 2 microns and 120 microns.

19. An apparatus for preparing a biological sample for analysis, the apparatus comprising:
 a film transportation device configured to move a continuous substrate film past a sample applicator unit; and,
 a sample applicator unit including one or more sample applicators configured to apply a trace of a biological sample to be analyzed onto the continuous substrate film when moved by the film transportation device, wherein the biological sample includes cells and wherein the trace of a biological sample forms substantially a monolayer of cells on a surface of the continuous substrate film.

20. The apparatus of claim 19, wherein the continuous substrate film includes a coating applied to a surface of the continuous substrate film onto which the trace of a biological sample for analysis is to be deposited to improve adherence of the trace of the biological sample.

* * * * *

UNITED STATES PATENT AND TRADEMARK OFFICE
CERTIFICATE OF CORRECTION

| | |
|---|---|
| PATENT NO. | : 10,379,014 B2 |
| APPLICATION NO. | : 15/356694 |
| DATED | : August 13, 2019 |
| INVENTOR(S) | : Andreas Calatzis and Harald Leyser |

Page 1 of 1

It is certified that error appears in the above-identified patent and that said Letters Patent is hereby corrected as shown below:

In the Specification

In Column 9, Line 61, before "e.g.,", insert --(--.

In Column 11, Line 49, before "e.g.,", insert --(--.

In Column 12, Line 43, after "µl", insert --,-- (first occurrence).

In Column 12, Line 54, delete "(ul/sec)" and insert --(µl/sec)--, therefor.

In Column 14, Line 15, delete "polyimide. (PA)" and insert --polyamide (PA),--, therefor.

In Column 18, Line 17, after "together", insert --to allow--.

In Column 18, Line 37, before "e.g.,", insert --(--.

Signed and Sealed this
Eighteenth Day of February, 2020

Andrei Iancu
*Director of the United States Patent and Trademark Office*